(12) United States Patent
Kamohara et al.

(10) Patent No.: US 6,291,546 B1
(45) Date of Patent: *Sep. 18, 2001

(54) SILICONE COMPOSITION FOR ORAL MUCOSA IMPRESSION

(75) Inventors: Hiroshi Kamohara; Makiko Takeo, both of Tokyo (JP)

(73) Assignee: GC Corporation, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/306,799

(22) Filed: May 7, 1999

(30) Foreign Application Priority Data

May 20, 1998 (JP) ................................. 10-153685

(51) Int. Cl.$^7$ .............. A61K 6/10; C08K 3/34; C08K 3/22; C08K 3/40; C08L 83/07
(52) U.S. Cl. .................... 523/109; 106/35; 433/214; 524/403; 524/442; 524/494; 524/506; 524/731; 524/862; 524/863; 528/32
(58) Field of Search ............... 523/109; 524/403, 524/442, 506, 731, 862, 494, 863; 528/32; 106/35; 433/214

(56) References Cited

U.S. PATENT DOCUMENTS

| | | |
|---|---|---|
| 4,550,030 | 10/1985 | Ohi et al. . |
| 4,604,142 | 8/1986 | Kamohara et al. . |
| 4,814,011 | 3/1989 | Kamohara et al. . |
| 4,909,847 | 3/1990 | Ohi et al. . |
| 4,911,759 | 3/1990 | Ohi et al. . |
| 5,203,914 | 4/1993 | Futami et al. . |
| 5,631,320 | 5/1997 | Kamohara et al. . |
| 5,637,628 | 6/1997 | Kamohara et al. . |
| 5,907,002 | 5/1999 | Kamohara et al. . |

FOREIGN PATENT DOCUMENTS

10072307A * 3/1998 (JP) .

* cited by examiner

Primary Examiner—Peter Szekely
(74) Attorney, Agent, or Firm—Oblon, Spivak, McClelland, Maier & Neustadt, P.C.

(57) ABSTRACT

A silicone composition for oral mucosa impression is disclosed, comprising:

(A) 100 parts by weight of an organopolysiloxane having at least two aliphatic unsaturated hydrocarbons in one molecule and having a viscosity at 25° C. of 500~1,500 cS;

(B) from 0.1 to 20 parts by weight of an organohydrogen polysiloxane having at least three hydrogen atoms directly bonded to a silicon atom in one molecule;

(C) from 10 to 500 ppm, based on the total amount of the components (A) and (B), of a silicone-soluble platinum compound;

(D) from 1 to 20 parts by weight of a linear methylphenyl polysiloxane having a viscosity at 25° C. of 30 to 10,000 cS;

(E) from 10 to 200 parts by weight of an inorganic filler; and (F) from 0.5 to 5 parts by weight of one or two or more surfactants selected from nonionic surfactants.

The silicone composition for coral mucosa impression according to the invention does not apply an excessive pressure causing a deformation of an oral mucosa at the time of impression taking, does not substantially flow in a portion to which no pressure is applied, and does not come into the innermost of a throat. Further, it does not have an irritation to the oral mucosa at all.

2 Claims, No Drawings

SILICONE COMPOSITION FOR ORAL MUCOSA IMPRESSION

BACKGROUND OF THE INVENTION

1. Field of the Invention

The present invention relates to a silicone composition for oral mucosa impression, which is used for undergoing oral mucosa impression taking with a good accuracy in the preparation or adjustment of dentures in the dentistry.

2. Description of the Related Art

In the dentistry, it is necessary to precisely reproduce the shape of an oral mucosa at the time of preparation or adjustment of a denture. If the shape of an oral mucosa is not precisely reproduced, the fittness between a denture base and an oral mucosa is lost, the denture likely becomes inferior in stability. As the result, when a patient masticates, not only the patient feels a pain on the oral mucosa, but also the mastication itself may become impossible with the denture coming out from the oral mucosa when the patient opens his or her mouth. For these reasons, there have been made various efforts for obtaining impression of the shape of an oral mucosa with a good accuracy using various impression materials. However, there are still various problems as described below, and the present state is that the impression taking with a good accuracy is not carried out.

In order to obtain the oral mucosa impression with a good accuracy, it is a necessary condition that in the impression taking, an impression material impresses precisely the shape of an oral mucosa without deforming the oral mucosa. For this, in bringing the impression material press-contacted with the oral mucosa, it is necessary to make a pressure to be applied to the mucosa press as low as possible. As the impression materials capable of obtaining the impression without applying an excessive pressure to the oral mucosa, there has since long been known a zinc oxide eugenol-based impression material. However, since this impression material has an irritation to the oral mucosa and gives an extreme pain to a patient at the time of impression taking, it is hardly used at the present time. For these reasons, dental impression materials developed mainly for the impression taking of crowns, bridges, and the like, such as an alginate, a polysulfide polymer, and a silicone, are usually used. However, since these impression materials do not flow unless a relatively high pressure is applied, an excessive pressure is applied to the oral mucosa at the time of impression taking, resulting in an incomplete impression with an inferior accuracy. In addition, the majority of patients who set a denture is a relatively aged person and is low to a vomiting reaction. Thus, in case of an impression material that readily flows spontaneously, there may be a danger that the impression material comes into the innermost part of a throat at the time of press contact.

Accordingly, in order to effect the oral mucosa impression taking with a good accuracy, an impression material is required to have such properties that although it flows by a very low pressure upon which the oral mucosa does not cause deformation, it does not come into the innermost part of a throat. Even materials having such properties can not be put into actual use if they have a large irritation to the mucosa.

SUMMARY OF THE INVENTION

Thus, an object of this invention is to provide an impression material for oral mucosa impression taking, having such properties that it flows by a very low pressure; in case where no pressure is applied, it does not substantially flow; and that it has a very low irritation to an oral mucosa.

In order to attain this object, the present inventors made extensive and intensive investigations. As a result, it has been found that if an organopolysiloxane having at least two aliphatic unsaturated hydrocarbons in one molecule and having a specified viscosity, an organohydrogen polysiloxane having at least three hydrogen atoms directly bonded to a silicon atom in one molecule, a silicone-soluble platinum compound, a linear methylphenyl polysiloxane having a specified viscosity, an inorganic filler, and a surfactant are compounded with each other in a specified ratio, owing to a mutual effect among the organopolysiloxane having a specified viscosity, the linear methylphenyl polysiloxane having a specified viscosity, and the surfactant, a silicone composition for oral mucosa impression that flows by a marked low pressure as compared with impression materials which have hitherto been used in the dentistry, does not substantially flow in a portion to which no pressure is applied, and that does not have an irritation to an oral mucosa, can be obtained, leading to accomplishment of this invention.

That is, the silicone composition for oral mucosa impression according to this invention comprises:

(A) 100 parts by weight of an organopolysiloxane having at least two aliphatic unsaturated hydrocarbons in one molecule and having a viscosity at 25° C. of 500~1,500 cS;

(B) 0.1~20 parts by weight of an organohydrogen polysiloxane having at least three hydrogen atoms directly bonded to a silicon atom in one molecule;

(C) 10~500 ppm, based on the total amount of the components (A) and (B), of a silicone-soluble platinum compound;

(D) 1~20 parts by weight of a linear methylphenyl polysiloxane having a viscosity at 25° C. of 30~10,000 cS;

(E) 10~200 parts by weight of an inorganic filler; and (F) 0.5~5 parts by weight of one or more than two surfactants selected from nonionic surfactants.

DETAILED DESCRIPTION OF THE INVENTION (A) As the organopolysiloxane having at least two aliphatic unsaturated hydrocarbons in one molecule and having a viscosity at 25° C. of 500~1,500 cS, the preferred organopolysiloxane are linear and terminated by vinylsilyl groups at the both ends of the molecular chain thereof. This terminal vinyl group may be present in the plural number, and the vinyl group may be included in the chain. This organopolysiloxane is a base material, and for its kneaded impression material to have such properties as it flows by a very low pressure, the viscosity at 25° C. must be from 500 to 1,500 cS. If the viscosity at 25° C. of the organopolysiloxane is lower than 500 cS, the resulting set material is brittle, whereas if it exceeds 1,500 cS, the pressure by which the kneaded impression material flows is too high. Accordingly, the both cases it is not suitable for the oral mucosa impression taking.

(B) The organohydrogen polysiloxane having at least three hydrogen atoms directly bonded to a silicon atom in one molecule functions as a crosslinking agent and is required to have at least three hydrogen atoms directly bonded to a silicon atom in a molecule thereof. If the amount of the organohydrogen polysiloxane is less than 0.1 part by weight based on 100 parts by weight of the component (A), not only the hardness of a set material is lowered, but the setting rate is slow, whereas if it exceeds 20 parts by weight, when a kneaded impression material comes into contact with the oral mucosa, the setting extremely proceeds so that the impression material is set while it flows on the mucosa. Accordingly, in the both cases it is not suitable for the oral mucosa impression taking.

(C) Examples of the silicone-soluble platinum compound include known addition reaction catalysts such as chloroplatinate, alcohol-modified chloroplatinate, and a complex of chloroplatinate with an olefin. In particular, a chloroplatinate-vinylsiloxane complex is preferably used. A suitable amount of the component (C) is in the range of 10~500 ppm based on the total amount of the components (A) and (B). If the amount of the component (C) is less than 10 ppm, the setting rate is slow, and in case where a trace amount of a substance which hinders the catalytic ability of the platinum compound is present, the setting becomes slow. On the other hand, if it exceeds 500 ppm, not only the setting rate is too fast, but the production cost is high, resulting in an economic disadvantages. Incidentally, it is preferred to use the silicone-soluble platinum compound such as chloroplatinate after being dissolved in an alcohol-, ketone-, ether- or hydrocarbon-based solvent, a polysiloxane oil, etc.

(D) The linear methylphenyl polysiloxane having a viscosity at 25° C. of 30~10,000 cS has such properties that when it is present together with the above-described organopolysiloxane having a specified viscosity as the component (A), it suppresses the spontaneously flow of an impression material without increasing the viscosity thereof, resulting in markedly lowering the flow of a portion to which no pressure is applied. Also, in many cases, the one or more than two surfactants selected from nonionic surfactants as described hereunder as the component (F) contain trace amounts of impurities, and when the impurities come into contact with an oral mucosa, they are liable to irritate the oral mucosa. Since the linear methylphenyl polysiloxane as the component (D) has a relatively good compatibility with organic matters, it has an effect such that it takes the impurities therein, thereby preventing the impurities to come into contact with the oral mucosa. The component (D) must have a viscosity at 25° C. of 30~10,000 cS. If the viscosity is less than 30 cS, or it exceeds 10,000 cS, bleeding from a set material occurs. Accordingly, the both cases are not proper. In addition, the component (D) is used in an amount of 1~20 parts by weight based on 100 parts by weight of the component (A). If the amount of the component (D) is less than 1 part by weight, the spontaneous flow of an impression material is large, whereas if it exceeds 20 parts by weight, the hardness of a set material is remarkably lowered. Accordingly, the both cases are not suitable.

(E) As the inorganic filler are used quartz, cristobalite, diatomaceous earth, fused quartz, glass fibers, titanium dioxide, fumed silica, and the like. The inorganic filler may be used in an amount of 10~200 parts by weight based on 100 parts by weight of the component (A). If the amount of the component (E) is less than 10 parts by weight, a set material is brittle, whereas if it exceeds 200 parts by weight, the viscosity of an impression material is too high, whereby the resistance at the time of kneading of the impression material becomes excessively large. Accordingly, the both cases are not suitable as the impression material.

(F) Suitable examples of the one or more than two surfactants selected from nonionic surfactants include nonionic surfactants wherein an alkyl group as a lipophilic group is combined with a hydrophilic group and nonionic surfactants wherein a fluorocarbon group in which hydrogen (s) in an alkyl group as a lipophilic group is substituted with fluorine(s) is combined with a hydrophilic group. In particular, the nonionic surfactant improves the wettability of a kneaded impression material to an oral mucosa, thereby improving the flow of the impression material at a moment when the impression material comes into contact with the oral mucosa. Thus, the surfactant as the component (F) taken together with the component (A) can give optimum fluid characteristics for the oral mucosa impression, namely characteristics of the impression material flowing by an extremely low pressure.

Examples of the nonionic surfactants wherein an alkyl group as a lipophilic group is combined with a hydrophilic group, which can be used as the surfactant of this invention, include:

(1) ether types wherein the number of added molecules of ethylene oxide or propylene oxide is 1~30, and the number carbons of the alkyl group is 12~22, such as polyoxyethylene alkyl ethers, polyoxypropylene alkyl ethers, and polyoxyethylene alkyl phenyl ethers;

(2) partial ester types of a polyhydric alcohol and a fatty acid having 12~22 carbon atoms, such as sorbitan fatty acid esters, glycerin fatty acid esters. polyglycerin fatty acid esters, ethylene glycol fatty acid esters, polyethylene glycol fatty acid esters, propylene glycol fatty acid esters, and pentaerythritol fatty acid esters;

(3) ether ester types wherein the number of added molecules of ethylene oxide is 1~30, and the number of carbons of a fatty acid is 12~22, such as polyoxyethylene sorbitan fatty acid esters, polyoxyethylene sorbitole fatty acid esters, polyoxyethylene mannitan fatty acid esters, polyoxyethylene glycerin fatty acid esters, and polyoxyethylene propylene glycol monohydric fatty acid esters; and (4) ester types with an ethylene oxide having the number of added molecules of 1~30, such as polyoxyethylene castor oil-hardened castor oil, polyoxyethylene lanolin derivatives, and polyoxyethylene beeswax derivatives.

Examples of the nonionic surfactants wherein a fluorocarbon group in which hydrogen(s) in an alkyl group as a lipophilic group is substituted with fluorine(s) is combined with a hydrophilic group include those represented by the following general formulae:

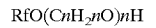

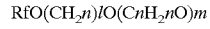

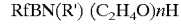

wherein Rf is a fluorinated aliphatic group or a fluorinated aromatic group each having 1~20 carbon atoms, which may be linear, branched, or cyclic; B is a divalent linking group (e.g., —$SO_2$—, —CO—, etc.); R' is a hydrogen atom or an alkyl group having 1~20 carbon atoms; and l, m, and n are each an integer of 1~50.

The surfactant as the component (F) has an effect for imparting hydrophilicity, and as the amount of the component (F) to be compounded is large, the hydrophilicity effect can be increased. However, if the amount of the component (F) to be compounded exceeds 5 parts by weight, the storage stability is lowered, whereas if it is less than 0.5 part by weight, the satisfactory effect for imparting hydrophilicity can not be obtained. For these reasons, the amount of the component (F) to be compounded must be in the range of 0.5~5 parts by weight based on 100 parts by weight of the component (A). Incidentally, the surfactant may be used singly or in admixture of two or more thereof.

In addition, so far as the characteristics of the silicone composition for oral mucosa impression according to this invention are not lost, various inorganic or organic coloring agents can be used. Examples oa the coloring agents which can be used include ones usually used for silicone compositions, such as red oxide, titanium white, titanium yellow, and cobalt blue.

This invention is described below in detail with reference to the following Examples, but it should not be construed that the invention is limited thereto.

EXAMPLE 1

A base paste and a catalyst paste having the following compositions were prepared.

| Base Paste: | |
| --- | --- |
| Dimethyl polysiloxane terminated by a methylvinyl siloxy group at the both ends of the molecular chain, having a viscosity at 25° C. of 500 cS | 100 parts by weight |
| Linear methylhydrogen polysiloxane having a methylhydrogen siloxane unit of 20 mole % | 3 parts by weight |
| Linear methylphenyl polysiloxane (viscosity at 25° C.: 10,000 cS) | 1 parts by weight |
| Quartz | 5 parts by weight |
| Polyoxyethylene nonyl phenyl ether | 1 part by weight |
| Catalyst paste: | |
| Dimethyl polysiloxane terminated by a dimethylvinyl siloxy group at the both ends of the molecular chain, having a viscosity at 25° C. of 500 cS | 100 parts by weight |
| Silicone oil solution containing 0.4% by weight of a 1,3-divinyltetramethyl disiloxane-platinum complex | 3 parts by weight |
| Linear methylphenyl polysiloxane (viscosity at 25° C.: 10,000 cS) | 1 part by weight |
| Quartz | 5 parts by weight |

With respect to the pressure, equal amount of the base paste and the catalyst paste were kneaded with each other for 30 seconds by means of spatula, and a cylindrical metal piece having a 2 cm in diameter×2 mm in height was penetrated into the kneaded material at a rate of travel of 20 mm/sec by means of a dynamic wettability tester (manufactured by Rhesca Company, Limited), whereby a pressure applied to the metal piece was measured. Also, with respect to the spontaneous flow of the kneaded material, since no general test method is defined, in this invention, after filing a material kneaded according to the consistency test method of the "Dental Rubbery Elastic Impression Materials" as refined in JIS T6513, in a cylinder having a diameter of 10 mm, 5 cc of the resulting kneaded material was extruded on a glass sheet and allowed to stand for setting, whereby its spontaneously enlarged diameter was measured for evaluation. In this evaluation method, when the spontaneously enlarged diameter is 11 mm or smaller, the inventors have already confirmed that the kneaded material has characteristics that no spontaneous flow occurs from the actual clinical viewpoint. Further, the evaluation of irritation to an oral mucosa and the evaluation of an accuracy of impression were made in terms of a degree of irritation and by observation of an impression surface, respectively after undergoing the actual oral mucosa impression taking. The results obtained are shown in Table 1.

As shown in Table 1, the pressure applied to the metal piece was about ½ of that in commercially available impression materials having a large flow used as comparative examples (Comparative Examples 2 and 3). Also, with respect to the spontaneous flow, the measured value was close to the diameter of the cylinder, and the spontaneous flow did not substantially occur. And, no irritation to the oral mucosa was observed, and the accuracy of impression was good.

EXAMPLE 2

A base paste and a catalyst paste having the following compositions were prepared.

| Base Paste: | |
| --- | --- |
| Dimethyl polysiloxane terminated by a methylvinyl siloxy group at the both ends of the molecular chain, having a viscosity at 25° C. of 1,500 cS | 100 parts by weight |
| Linear methylhydrogen polysiloxane having a methylhydrogen siloxane unit of 20 mole % | 40 parts by weight |
| Linear methylphenyl polysiloxane (viscosity at 25° C.: 30 cS) | 20 parts by weight |
| Fused quartz | 200 parts by weight |
| Polyoxyethylene sorbitan fatty acid ester | 5 parts by weight |
| Catalyst paste: | |
| Dimethyl polysiloxane terminated by a dimethylvinyl siloxy group at the both ends of the molecular chain, having a viscosity at 25° C. of 1,500 cS | 100 parts by weight |
| Silicone oil solution containing 0.4% by weight of a 1,3-divinyltetramethyl disiloxane-platinum complex | 5 parts by weight |
| Linear methylphenyl polysiloxane (viscosity at 25° C.: 30 cS) | 20 parts by weight |
| Fused quartz | 200 parts by weight |

Equal amount of the base paste and the catalyst paste were kneaded with each other for 30 seconds by means of a spatula, and the same tests as in Example 1 were carried out. The results obtained are shown in Table 1.

As shown in Table 1, the pressure applied to the metal piece was about ½ of that in commercially available impression materials having a large flow used as comparative examples (Comparative Examples 2 and 3). Also, with respect to the spontaneous flow, the measured value was close to the diameter of the cylinder, and the spontaneous flow did not substantially occur. And, no irritation to the oral mucosa was observed, and the accuracy of impression was good.

EXAMPLE 3

A base paste and a catalyst paste having the following compositions were prepared.

| Base Paste: | |
| --- | --- |
| Dimethyl polysiloxane terminated by a methylvinyl siloxy group at the both ends of the molecular chain, having a viscosity at 25° C. of 1,000 cS | 100 parts by weight |
| Linear methylhydrogen polysiloxane having a methylhydrogen siloxane unit of 20 mole % | 10 parts by weight |
| Linear methylphenyl polysiloxane (viscosity at 25° C.: 1,000 cS) | 10 parts by weight |
| Quartz | 100 parts by weight |

-continued

| | |
|---|---|
| Polyethylene glycol fatty acid ester | 10 parts by weight |
| Catalyst paste: | |
| Dimethyl polysiloxane terminated by a dimethylvinyl siloxy group at the both ends of the molecular chain, having a viscosity at 25° C. of 1,000 Cs | 100 parts by weight |
| Silicone oil solution containing 0.4% by weight of a 1,3-divinyltetramethyl disiloxane-platinum complex | 5 parts by weight |
| Linear methylphenyl polysiloxane (viscosity at 25° C.: 1,000 cS) | 10 parts by weight |
| Quartz | 100 parts by weight |

Equal amount of the base paste and the catalyst paste were kneaded with each other for 30 seconds by means of a spatula, and the same tests as in Example 1 were carried out. The results obtained are shown in Table 1.

As shown in Table 1, the pressure applied to the metal piece was about ½ of that in commercially available impression materials having a large flow used as comparative examples (Comparative Examples 2 and 3). Also, with respect to the spontaneous flow, the measured value was close to the diameter of the cylinder, and the spontaneous flow did not substantially occur. And, no irritation to the oral mucosa was observed, and the accuracy of impression was good.

Comparative Example 1

A base paste and a catalyst paste having the following compositions were prepared.

| | |
|---|---|
| Base Paste: | |
| Dimethyl polysiloxane terminated by a methylvinyl siloxy group at the both ends of the molecular chain, having a viscosity at 25° C. of 10,000 cS | 100 parts by weight |
| Linear methylhydrogen polysiloxane having a methylhydrogen siloxane unit of 20 mole % | 10 parts by weight |
| Quartz | 100 parts by weight |
| Polyoxyethylene nonyl phenyl ether | 10 parts by weight |
| Catalyst paste: | |
| Dimethyl polysiloxane terminated by a dimethylvinyl siloxy group at the both ends of the molecular chain, having a viscosity at 25° C. of 10,000 Cs | 100 parts by weight |
| Silicone oil solution containing 0.4% by weight of a 1,3-divinyltetramethyl disiloxane-platinum complex | 5 parts by weight |
| Quartz | 100 parts by weight |

Equal amount of the base paste and the catalyst paste were kneaded with each other for 30 seconds by means of a spatula, and the same tests as in Example 1 were carried out. The results obtained are shown in Table 1.

As shown in Table 1, the pressure applied to the metal piece was substantially equal to that in commercially available impression used as comparative examples (Comparative Examples 2 and 3). Also, the spontaneous flow was large. Further, the irritation to the oral mucosa was slightly observed, and the accuracy of impression was rather inferior.

Comparative Example 2

Using a commercially available silicone impression material, "GC Exafine Injection Type" (made by GC Corporation), equal amount of a base paste and a catalyst paste were kneaded with each other for 30 seconds by means of a spatula, and the same tests as in Example 1 were carried out. The results obtained are shown in Table 1.

As shown in Table 1, the pressure applied to the metal piece was approximately two times that of Examples 1 to 3. Also, the spontaneous flow was large. Further, the irritation to the oral mucosa was slightly observed, and the accuracy of impression was rather inferior.

Comparative Example 3

Using a commercially available zinc, oxide eugenol-based impression material, "GC Impression Paste Hard" (made by GC Corporation), equal amount of a pink paste and a brown paste were kneaded with each other for 30 seconds by means of a spatula, and the same tests as in Example 1 were carried out. The results obtained are shown in Table 1.

As shown in Table 1, the pressure applied to the metal piece was higher than that in the compositions of Examples 1 to 3. Also, the spontaneous flow was large. Further, the irritation to the oral mucosa was very large, and the accuracy of impression was slightly poor.

TABLE 1

| | Example 1 | Example 2 | Example 3 | Comparative Example 1 | Comparative Example 2 | Comparative Example 3 |
|---|---|---|---|---|---|---|
| Pressure (mN) | 20 | 21 | 19 | 42 | 43 | 32 |
| Spontaneous flow (mm) | 10 | 11 | 10 | 25 | 30 | 28 |
| Irritation to oral mucosa* | A | A | A | B | B | C |
| Accuracy of impression | Good | Good | Good | Slightly inferior | Slightly inferior | Slightly inferior |

A: The irritation was not observed at all.
B: The irritation was slightly observed.
C: The irritation was largely observed.

As is evident from Table 1, in the silicone compositions for oral mucosa impression according to this invention, since the pressure applied to the metal piece was about ½ of that in the commercially available silicone impression materials as used in the Comparative Examples, it can be understood that the pressure applied to the oral mucosa at the time of impression taking is very low. Also, with respect to the spontaneous flow, the measured values were substantially equal to the diameter of the cylinder as used for the measurement, and it was confirmed that the spontaneous flow did not substantially occur. On the other hand, in each of the Comparative Examples including those of commercially available impression materials, the pressure and the spontaneous flow were considerably high as compared with those in each of the Examples. At the time of the actual impression taking, there are fears that an excessive pressure is applied to the oral mucosa and that the impression material comes into a throat due to the spontaneous flow. Accordingly, it was confirmed that these impression materials of the Comparative Examples were not suitable for the oral mucosa impression.

In addition, in the composition in each of the Examples, the irritation to the oral mucosa was not observed at all, and the accuracy of impression was good. On the other hand, in each of the Comparative Examples, the irritation to the oral mucosa was observed, and the accuracy of impression was inferior. In particular, the zinc oxide eugenol-based impression material of Comparative Example 3, a very large irritation to the oral mucosa was observed.

In the light of the above, the silicone composition for oral mucosa impression according to this invention does not apply an excessive pressure to the oral mucosa at the time of impression taking, and since the kneaded material in a portion to which no pressure is applied hardly flows, it does not come into the innermost of a throat. Further, it does not have an irritation to the oral mucosa at all. Because of these characteristics, the silicone composition for oral mucosa impression according to this invention can take the impression of the oral mucosa with an extremely good accuracy and is markedly superior as an impression material exclusively for the oral mucosa at the time of preparation or adjustment of dentures. Thus, this invention greatly contributes to the dental field.

While the invention has been described in detail and with reference to specific embodiments thereof, it will be apparent to one skilled in the art that various changes and modifications can be made therein without departing from the spirit and scope thereof.

What is claimed is:

1. A silicone composition for oral mucosa impression comprising:

(A) 100 parts by weight of an organopolysiloxane having at least two aliphatic unsaturated hydrocarbons in one molecule and having a viscosity at 25° C. of 500–1,500 cS;

(B) from 0.1 to 20 parts by weight of an organohydrogen polysiloxane having at least three hydrogen atoms directly bonded to a silicon atom in one molecule;

(C) from 10 to 500 ppm, based on the total amount of the components (A) and (B), of a silicone-soluble platinum compound;

(D) from 1 to 20 parts by weight of a linear methylphenyl polysiloxane having a viscosity at 25° C. of from 30 to 10,000 cS;

(E) from 10 to 200 parts by weight of an inorganic filler selected from the group consisting of quartz, cristbalite, diatomaceous earth, fused quartz, glass fibers, titanium dioxide, and fumed silica; and (F) from 0.5 to 5 parts by weight of at least one surfactant selected from nonionic surfactants.

2. A silicone composition of claim 1, comprising from 1 to 10 parts by weight of said linear methylphenyl polysiloxane having a viscosity at 25° C. of from 30 to 10,000 cS.

* * * * *